United States Patent
Nolte et al.

(10) Patent No.: US 9,451,767 B2
(45) Date of Patent: Sep. 27, 2016

(54) AQUEOUS COMPOSITION COMPRISING DICAMBA AND A DRIFT CONTROL AGENT

(71) Applicant: BASF SE, Ludwigshafen (DE)

(72) Inventors: Marc Nolte, Mannheim (DE); Wen Xu, Cary, NC (US); Steven Bowe, Apex, NC (US); Maarten Staal, Durham, NC (US); Terrance M. Cannan, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 101 days.

(21) Appl. No.: 14/408,172

(22) PCT Filed: Jun. 11, 2013

(86) PCT No.: PCT/EP2013/061962
§ 371 (c)(1),
(2) Date: Dec. 15, 2014

(87) PCT Pub. No.: WO2013/189773
PCT Pub. Date: Dec. 27, 2013

(65) Prior Publication Data
US 2015/0173354 A1    Jun. 25, 2015

Related U.S. Application Data

(60) Provisional application No. 61/662,390, filed on Jun. 21, 2012.

(30) Foreign Application Priority Data

Jul. 5, 2012  (EP) .................................. 12175090

(51) Int. Cl.
| | | |
|---|---|---|
| *A01N 37/44* | (2006.01) |
| *A01N 33/04* | (2006.01) |
| *A01N 37/40* | (2006.01) |
| *A01N 37/10* | (2006.01) |

(52) U.S. Cl.
CPC ................ *A01N 33/04* (2013.01); *A01N 37/10* (2013.01); *A01N 37/40* (2013.01); *A01N 37/44* (2013.01)

(58) Field of Classification Search
CPC ........................................................ A01N 37/44
USPC ........................................................... 514/564
See application file for complete search history.

(56) References Cited

FOREIGN PATENT DOCUMENTS

| | | |
|---|---|---|
| WO | WO 02/34047 | 5/2002 |
| WO | WO 03/103396 | 12/2003 |
| WO | WO 2010/051435 | 5/2010 |
| WO | WO 2011/019652 | 2/2011 |
| WO | WO 2011/010211 | 9/2011 |
| WO | WO 2012/076567 | 6/2012 |

OTHER PUBLICATIONS

International Search Report dated Jul. 12, 2013, prepared in International Application No. PCT/EP2013/061962.
International Preliminary Report on Patentability dated Jun. 6, 2014, prepared in International Application No. PCT/EP2013/061962.

*Primary Examiner* — Raymond Henley, III
(74) *Attorney, Agent, or Firm* — Brinks Gilson & Lione

(57) ABSTRACT

The present invention relates to an aqueous composition comprising dicamba and a drift control agent; to a method for preparing a tank mix, which comprises the step of contacting water and said composition, and optionally further pesticides; to a method of controlling phytopathogenic fungi and/or undesired vegetation and/or unde-sired insect or mite attack and/or for regulating the growth of plants, wherein the composition is allowed to act on the respective pests, their environment or the plants to be protected from the respective pest, on the soil and/or on undesired plants and/or the crop plants and/or their environment; and finally to a use of the alkoxylate of the formula (I) as defined below for reducing the wind drift of an aqueous composition comprising a pesticide.

19 Claims, No Drawings

AQUEOUS COMPOSITION COMPRISING DICAMBA AND A DRIFT CONTROL AGENT

This application is a National Stage application of International Application No. PCT/EP2013/061962, filed Jun. 11, 2013, which claims the benefit of U.S. Provisional Application No. 61/662,390, filed Jun. 21, 2012, the entire contents of which are hereby incorporated herein by reference. This application also claims priority under 35 U.S.C. §119 to European Patent Application No. 12175090.5, filed Jul. 5, 2012, the entire contents of which is hereby incorporated herein by reference.

The present invention relates to an aqueous composition comprising dicamba and a drift control agent; to a method for preparing a tank mix, which comprises the step of contacting water and said composition, and optionally further pesticides; to a method of controlling phytopathogenic fungi and/or undesired vegetation and/or undesired insect or mite attack and/or for regulating the growth of plants, wherein the composition is allowed to act on the respective pests, their environment or the plants to be protected from the respective pest, on the soil and/or on undesired plants and/or the crop plants and/or their environment; and finally to a use of the alkoxylate of the formula (I) as defined below for reducing the wind drift of an aqueous composition comprising a pesticide. The preferred embodiments of the invention mentioned herein below have to be understood as being preferred either independently from each other or in combination with one another.

The reduction wind drift is an important object in agrochemistry. Various drift control agents are known showing a wide variety of different chemical compositions. Thus, it is very difficult to identify new drift control agents or optimizing structures of known drift control agents.

Dicamba is an important herbicide, which requires high drift control to avoid damages in neighboring fields.

Object of the present invention was to find a new drift control agent with improved properties. These agents should be easily to prepare starting from cheap, industrially available compounds, which are easy to handle. Yet another object was to find a dicamba composition, which allows a high drift control.

The object was solved by an aqueous composition comprising dicamba and a drift control agent. The object was also solved by a use of the alkoxylate of the formula (I) as defined below for reducing the wind drift of aqueous composition comprising a pesticide.

Drift control agents may be understood as chemical agents, which reduce the wind drift when spraying an aqueous tank mix composition. Drift control agents are commercially available from various companies (tradenames of the products given in brackets): Ag Spray, Inc. (Halt), Ashland Specialty Ingredients (Soilcare), Brewer International Inc. (Poly Control 2), Conklin Co. Inc. (Complete), Helena Chemical Co. (AccuQuest WM, AccuZone DC, Grounded, On-Line, Sta Put, Strike Zone, LineMan), Intracrop (Driftless), Kalo, Inc. (One AP XL, Spectra Tank Mix, Spectra Max), Loveland Products, Inc. (LI 700), Nalco Co. (Staput Plus), Precision Laboratories, Inc. (Border, Border Xtra, Direct, Transport Plus), Rhodia Inc. (AgRHO DEP, AgRHO DR), Sanitek Products, Inc. (SANAG Div.) (41-A, 38-F), Willowood USA (Willowood Driftguard), FORMULATORS' TRADE NAMES: Brandt Consolidated, Inc. (Drift Free), Custom Agricultural Formulators (Driftstop), Loveland Products, Inc. (Compadre, Liberate, Reign, Reign LC, Weather Gard Complete), Wilbur-Ellis Co. (Bronc Max EDT, EDT Concentrate, In-Place), Winfield Solutions, LLC (Arrow four, Corral AMS, InterLock, Placement Propak, PowerLock), and various other discontinued commercial products, such as Apasil, Bivert, Chem-Trol, Confine, Corral Poly, Drifgon, Driftgard, Drop Zone, Intac Plus, Nalcotrol, Nalcotrol II, Nalquatic, Progacyl, Target, TMP, Wind-Fall.

Preferred examples of drift control agents are
lecithin derivatives,
linear nonionic polymers with a molecular weight of at least 20 kDa,
guar gum,
fatty alcohol alkoxylates.

Preferred drift control agents are the fatty alcohol alkoxylates.

Suitable lecithin derivatives are lecithin or its chemically modified derivatives. Such drift control agents are for example commercially available as Liberate® or Compadre® from Loveland Products.

Suitable linear nonionic polymers with a molecular weight of at least 20 kDa, may be selected from polyacrylamide, polyacrylate, or a polyethylene glycol. Preferred nonionic polymers are polyacrylamide and polyacrylate. The molecular weight of said nonionic polymers is usually at least 50 kDa, preferably at least 100 kDa, and in particular at least 1000 kDa.

Suitable guar gums are for example described in EP0660999, or are commercially available as AGRHO® DEP 775 or AGRHO® DR 200 from Rhodia.

Preferred fatty alcohol alkoxylates are fatty alcohol ethoxylates. The fatty alcohol may comprise a $C_{12\text{-}22}$, preferably a $C_{14\text{-}20}$, and in particular a $C_{16\text{-}18}$ fatty alcohol. The fatty alcohol ethoxylate may comprise from 1 to 15, preferably from 1 to 8, and in particular from 2 to 6 equivalents of ethylene oxide. Especially suitable fatty alcohol ethoxylate is a $C_{14\text{-}20}$ fatty alcohol, which comprises from 2 to 6 equivalents of ethylene oxide.

The drift control agent may have a HLB value of 4.0 to 11.0, preferably of 6.0 to 10.0 and in particular of 8.0 to 10.0. In another particular preferred form the drift control agent (such as the alkoxylate of the formula (I)) has a HLB of 5.0 to 8.0, and most preferably from 6.0 to 7.0. The HLB may be determined according to Griffin.

In an especially preferred form the drift control agent is a fatty alcohol alkoxylate, such as an alkoxylate of the formula (I)

$$R^a\text{—}O\text{—}(C_mH_{2m}\text{—}O)_n\text{—}H \qquad (I)$$

wherein $R^a$ is $C_8$-$C_{22}$-alkyl and/or -alkenyl, m is 2, 3, 4 or a mixture thereof, and n is from 1 to 15. The alkoxylates of the formula (I) are obtainable by common alkoxylation of alcohols $R^a$—OH, e.g. with ethylene oxide (resulting in m=2), propylene oxide, or butylene oxide.

$R^a$ may be an alkyl, alkenyl or a mixture thereof. Preferably $R^a$ is an alkenyl or a mixture of an alkenyl with an alkyl. In case $R_a$ contains an alkenyl said alkenyl may comprise at least one double bond. $R^a$ is preferably a $C_{12}$-$C_{20}$-alkyl and/or -alkenyl. More preferably $R^a$ is $C_{16}$-$C_{18}$-alkyl and/or -alkenyl. Especially preferred $R^a$ is oleyl and/or cetyl.

Preferably, m is 2, a mixture of 2 and 3, or a mixture of 2 and 4. In particular, m is 2.

Preferably, n is from 2 to 8. In particular, n is from 2 to 5.

In a very preferred form the drift control agent is an alkoxylate of the formula (I), wherein $R^a$ is $C_{12}$-$C_{20}$-alkyl and/or -alkenyl, m is 2, a mixture of 2 and 3, or a mixture of 2 and 4, and n is from 2 to 8. In an even more preferred form the drift control agent is an alkoxylate of the formula (I), wherein $R^a$ is $C_{16}$-$C_{18}$-alkyl and/or -alkenyl, m is 2, and n is from 2 to 5.

The composition contains usually at least 1 wt %, preferably at least 5 wt %, and in particular at least 10 wt % of the drift control agent. The composition contains usually up 50 wt %, preferably up to 30 wt %, and in particular up to 20 wt % of the drift control agent.

The aqueous composition according to the invention comprises dicamba and a drift control agent. Dicamba is a known herbicide, which may be present in form of an protonated acid, in form of a salt, or a mixture thereof. Various dicamba salts may be used, such as dicamba sodium, dicamba dimethylamine, dicamba diglycolamine. Dicamba is available in the commercial products like BANVEL®+2,4-D, BANVEL HERBICIDE®, BANVEL-K+ATRAZINE®, BRUSH-MASTER®, CELEBRITY PLUS®, CIMARRON MAX®, CLARITY HERBICIDE®, COOL POWER®, DIABLO HERBICIDE®, DICAMBA DMA SALT, DISTINCT HERBICIDE®, ENDRUN®, HORSEPOWER*®, LATIGO®, MARKSMAN HERBICIDE®, MACAMINE-D®, NORTHSTAR HERBICIDE®, OUTLAW HERBICIDE®, POWER ZONE®, PROKOZ VESSEL®, PULSAR®, Q4 TURF HERBICIDE®, RANGESTAR®, REQUIRE Q®, RIFLE®, RIFLE PLUS®, RIFLE-D®, SPEED ZONE®, STATUS HERBICIDE®, STER-LING BLUE®, STRUT®, SUPER TRIMEC*®, SURGE*®, TRIMEC BENTGRASS*®, TRIMEC CLASSIC*®, TRIMEC PLUS*®, TRIPLET SF®, TROOPER EXTRA®, VANQUISH®, VETERAN 720®, VISION HERBICIDE®, WEEDMASTER®, YUKON HERBICIDE®.

Preferably, dicamba is present in form of a dicamba polyamine salt and the polyamine has the formula (A1)

wherein
$R^1$, $R^2$, $R^4$, $R^6$, and $R^7$ are independently H or $C_1$-$C_6$-alkyl, which is optionally substituted with OH,
$R^3$ and $R^5$ are independently $C_2$-$C_{10}$-alkylene,
X is OH or $NR^6R^7$, and
n is from 1 to 20;
or the formula (A2)

wherein
$R^{10}$ and $R^{11}$ are independently H or $C_1$-$C_6$-alkyl,
$R^{12}$ is $C_1$-$C_{12}$-alkylene, and
$R^{13}$ is an aliphatic $C_5$-$C_8$ ring system, which comprises either nitrogen in the ring or which is substituted with at least one unit $NR^{10}R^{11}$.

The term "polyamine" within the meaning of the invention relates to an organic compound comprising at least two amino groups, such as an primary, secondary or tertiary amino group.

The dicamba polyamine salt usually comprises an anionic dicamba and a cationic polyamine. The term "cationic polyamine" refers to a polyamine, which is present as cation. Preferably, in a cationic polyamine at least one amino group is present in the cationic form of an ammonium, such as R—$N^+H_3$, $R_2$—$N^+H_2$, or $R_3$—$N^+H$. An expert is aware which of the amine groups in the cationic polyamine is preferably protonated, because this depends for example on the pH or the physical form. In aqueous solutions the alkalinity of the amino groups of the cationic polyamine increases usually from tertiary amine to primary amine to secondary amine.

In an embodiment the cationic polyamine has the formula

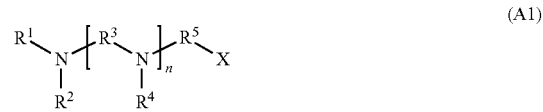

wherein $R^1$, $R^2$, $R^4$, $R^6$, $R^7$ are independently H or $C_1$-$C_6$-alkyl, which is optionally substituted with OH, $R^3$ and $R^5$ are independently $C_2$-$C_{10}$-alkylene, X is OH or $NR^6R^7$, and n is from 1 to 20. $R^1$, $R^2$, $R^4$, $R^6$ and $R^7$ are preferably independently H or methyl. Preferably, $R^1$, $R^2$, $R^6$ and $R^7$ are H. $R^6$ and $R^7$ are preferably identical to $R^1$ and $R^2$, respectively. $R^3$ and $R^5$ are preferably independently $C_2$-$C_3$-alkylene, such as ethylene (—$CH_2CH_2$—), or n-propylene (—$CH_2CH_2CH_2$—). Typically, $R^3$ and $R^5$ are identical. $R^3$ and $R^5$ may be linear or branched, unsubstituted or substituted with halogen. Preferably, $R^3$ and $R^5$ are linear. Preferably, $R^3$ and $R^5$ are unsubstituted. X is preferably $NR^6R^7$. Preferably, n is from 1 to 10, more preferably from 1 to 6, especially from 1 to 4. In another preferred embodiment, n is from 2 to 10. Preferably, $R^1$, $R^2$, and $R^4$ are independently H or methyl, $R^3$ and $R^5$ are independently $C_2$-$C_3$-alkylene, X is OH or $NR^6R^7$, and n is from 1 to 10.

The group X is bound to $R^5$, which is a $C_2$-$C_{10}$-alkylene group. This means that X may be bound to any carbon atom of the $C_2$-$C_{10}$-alkylene group. Examples of a unit —$R^5$—X are —$CH_2$—$CH_2$—$CH_2$—OH or —$CH_2$—CH(OH)—$CH_3$.
$R^1$, $R^2$, $R^4$, $R^6$, $R^7$ are independently H or $C_1$-$C_6$-alkyl, which is optionally substituted with OH. An example of a substitution is formula (B1.9), in which $R^4$ is H or $C_1$-$C_6$-alkyl substituted with OH (more specifically, $R^4$ is $C_3$-alkyl substituted with OH. Preferably, $R^1$, $R^2$, $R^4$, $R^6$, $R^7$ are independently H or $C_1$-$C_6$-alkyl.

In another preferred embodiment the cationic polymer of the formula (A1) is free of ether groups (—O—). Ether groups are known to enhance photochemical degradation resulting in explovixe radicals or peroxy groups.

Examples for cationic polyamines of the formula (A1) wherein X is $NR^6R^7$ are diethylenetriamine (DETA, (A4) with k=1, corresponding to (A1.1)), triethylenetetraamine (TETA, (A4) with k=2), tetraethylenepentaamine (TEPA, (A4) with k=3). Technical qualities of TETA are often mixtures comprising in addition to linear TETA as main component also tris-aminoethylamine TAEA, Piperazinoethylethylenediamine PEEDA and Diaminoethylpiperazine DAEP. Technical qualities of TEPA a are often mixtures comprising in addition to linear TEPA as main component also aminoethyltris-aminoethylamine AE-TAEA, aminoethyldiaminoethylpiperazine AE-DAEP and aminoethylpiperazinoethylethylenediamine AE-PEEDA. Such ethyleneamines are commercially available from Dow Chemical Company. Further examples are Pentamethyldiethylenetriamine PMDETA (B1.3), N,N,N',N",N"-pentamethyl-dipropylenetriamine (B1.4) (commercially available as Jeffcat® ZR-40), N,N-bis(3-dimethylaminopropyl)-N-isopropanolamine (commercially available as Jeffcat® ZR-50), N'-(3-(dimethylamino)propyl)-N,N-dimethyl-1,3-propanediamine (A1.5) (commercially available as Jeffcat® Z-130), and N,N-Bis(3-aminopropyl)methylamine BAPMA (A1.2). Especially preferred are (A4), wherein k is from 1 to 10, (A1.2), (A1.4) and (A1.5). Most preferred are (A4), wherein k is 1, 2, 3, or 4 and (A1.2). In particular preferred are (A1.1) and (A1.2), wherein the latter is most preferred.

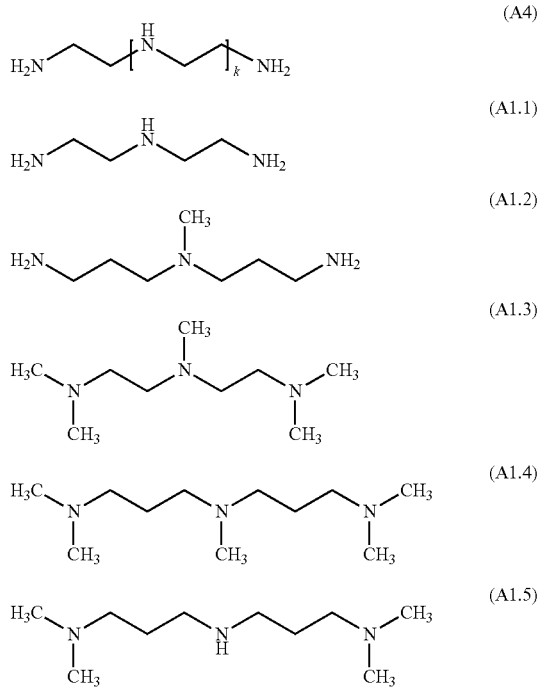

Examples for polyamines of the formula (A1) wherein X is OH are N-(3-dimethylaminopropyl)-N,N-diisopropanolamine DPA (A1.9), N,N,N'-trimethylaminoethyl-ethanolamine (A1.7) (commercially available as Jeffcat® Z-110), aminopropylmonomethylethanolamine APMMEA (A1.8), and aminoethylethanolamine AEEA (A1.6). Especially preferred is (A1.6).

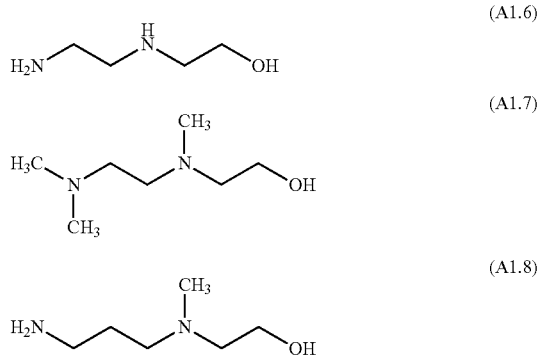

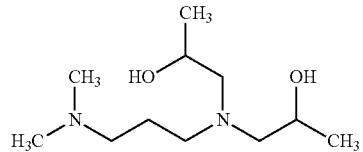

In another embodiment the cationic polyamine has the formula (A2)

$R^{10}$\\N/$R^{12}$—$R^{13}$\n|\n$R^{11}$ wherein $R^{10}$ and $R^{11}$ are independently H or $C_1$-$C_6$-alkyl, $R^{12}$ is $C_2$-$C_{12}$-alkylene, and $R^{13}$ is an aliphatic $C_5$-$C_8$ ring system, which comprises either nitrogen in the ring or which is substituted with at least one unit $NR^{10}R^{11}$.

$R^{10}$ and $R^{11}$ are preferably independently H or methyl, more preferably H. Typically $R^{10}$ and $R^{11}$ are linear or branched, unsubstituted or substituted with halogen. Preferably, $R^{10}$ and $R^{11}$ are unsubstituted and linear. More preferably, $R^{10}$ and $R^{11}$ are identical.

$R^{12}$ is preferably $C_2$-$C_4$-alkylene, such as ethylene (—$CH_2CH_2$—), or n-propylene (—$CH_2CH_2CH_2$—). $R^{12}$ may be linear or branched, preferably it is linear. $R^{12}$ may be unsubstituted or substituted with halogen, preferably it is unsubstituted.

$R^{13}$ is an aliphatic $C_5$-$C_8$ ring system, which comprises either nitrogen in the ring or which is substituted with at least one unit $NR^{10}R^{11}$. Preferably, $R^{13}$ is an aliphatic $C_5$-$C_8$ ring system, which comprises nitrogen in the ring. The $C_5$-$C_8$ ring system may be unsubstituted or substituted with at least one $C_1$-$C_6$ alkyl group or at least one halogen. Preferably, the $C_5$-$C_8$ ring system is unsubstituted or substituted with at least one $C_1$-$C_4$ alkyl group. Examples for an aliphatic $C_5$-$C_8$ ring system, which comprises nitrogen in the ring, are piperazyl groups. Examples for $R^{13}$ being an aliphatic $C_5$-$C_8$ ring system, which comprises nitrogen in the ring, are the compounds of the formulat (A2.11) and (A2.12) below. Examples for $R^{13}$ being an aliphatic $C_5$-$C_8$ ring system, which is substituted with at least one unit $NR^{10}R^{11}$ is the compound of the formula (A2.10) below.

More preferably, $R^{10}$ and $R^{11}$ are independently H or methyl, $R^{12}$ is $C_2$-$C_3$-alkylene, and $R^{13}$ is an aliphatic $C_5$-$C_8$ ring system, which comprises oxygen or nitrogen in the ring. In another preferred embodiment the cationic polymer of the formula (A2) is free of ether groups (—O—).

Especially preferred cationic polyamines of formula (A2) are isophorone diamine ISPA (A2.10), aminoethylpiperazine AEP (A2.11), and 1-methyl-4-(2-dimethylaminoethyl)piperazine TAP (A2.12). These compounds are commercially available from Huntsman or Dow, USA. Preferred are (A2.10) and (A2.11), more preferably (A2.11). In another embodiment (A2.11) and (A2.12) are preferred.

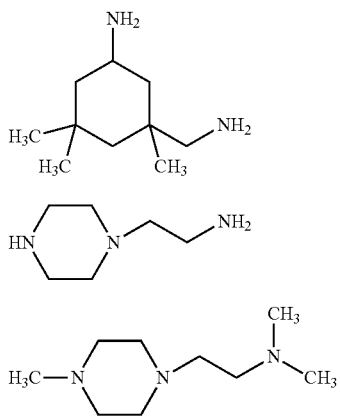

(A2.10)

(A2.11)

(A2.12)

Dicamba is most preferred present in form of a N,N-bis (3-aminopropyl)methylamine (so called "BAPMA") salt.

The composition contains usually at least 50 g/l, preferably at least 300 g/l, more preferably at least 400 g/l, and in particular at least 450 g/l acid equivalents (AE) of dicamba. The composition contains usually up to 800 g/l, preferably up to 700 g/l, more preferably up to 650 g/l, and in particular up to 600 g/l acid equivalents (AE) of dicamba.

The composition according to the invention is usually present in form of an homogenous solution, e.g. at 20° C. Typically, the dicamba and the drift control agent are dissolved in the aqueous composition.

In a preferred form the aqueous composition contains at least 300 g/l acid equivalents of dicamba (e.g. as dicamba salt of the polyamine of the formula (A1), at least 5 wt % of the drift control agent (e.g. the alkoxylate of the formula (I)), and water up to 100 wt %.

In a more preferred form the aqueous composition contains at least 400 g/l acid equivalents of dicamba (e.g. as dicamba BAPMA salt), at least 8 wt % of the drift control agent (e.g. the alkoxylate of the formula (I), wherein $R^a$ is $C_{16}$-$C_{18}$-alkyl and/or -alkenyl, m is 2, and n is from 2 to 5), and water up to 100 wt %.

The aqeuous composition may comprise additional pesticides in addition to dicamba. Suitable additional pesticides are pesticides as defined below. Preferred additional pesticides are herbicides, such as
  amino acid derivatives: bilanafos, glyphosate (e.g. glyphosate free acid, glyphosate ammonium salt, glyphosate isopropylammonium salt, glyphosate trimethylsulfonium salt, glyphosate potassium salt, glyphosate dimethylamine salt), glufosinate, sulfosate;
  imidazolinones: imazamethabenz, imazamox, imazapic, imazapyr, imazaquin, imazethapyr;
  phenoxy acetic acids: clomeprop, 2,4-dichlorophenoxyacetic acid (2,4-D), 2,4-DB, dichlorprop, MCPA, MCPA-thioethyl, MCPB, Mecoprop.

More preferred additional pesticides are glyphosate and 2,4-D. Most preferred additional pesticide is glyphosate.

The aqueous composition may comprise auxiliaries, such as solvents, liquid carriers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants.

Suitable solvents and liquid carriers are organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate. The alkoxylate of the formula (I) is not a nonionic surfactant within the meaning of this invention.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

The present invention further relates to a method for preparing a tank mix, which comprises the step of contacting water and the aqueous composition according to the invention, and optionally further pesticides.

The tank mix may contain up to 10 wt %, preferably up to 5 wt %, and in particular up to 2 wt % of the of the aqueous composition. Usually, the tank mix contains at least 0.1 wt % of the aqueous composition.

The tank mix may contain up to 3.0 wt %, preferably up to 0.5 wt %, and in particular up to 0.25 wt % of the of the drift control agent. Usually, the tank mix contains at least 0.01 wt % of the drift control agent.

The further pesticides may be selected from any pesticide. The term "pesticide" refers to at least one active substance selected from the group of the fungicides, insecticides, nematicides, herbicides, safeners and/or growth regulators. Preferred pesticides are herbicides. Mixtures of pesticides of two or more of the abovementioned classes may also be used. The skilled worker is familiar with such pesticides, which can be found, for example, in the Pesticide Manual, 15th Ed. (2009), The British Crop Protection Council, London. The following list give examples of pesticides which may be used as pesticide. Examples for fungicides are:

A) strobilurins azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

B) carboxamides carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide;

other carboxamides: carpropamid, dicyclomet, mandipropamid, oxytetracyclin, silthiofarm and N-(6-methoxy-pyridin-3-yl) cyclopropanecarboxylic acid amide;

C) azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, pefurazoate, prochloraz, triflumizol;

benzimidazoles: benomyl, carbendazim, fuberidazole, thiabendazole;

others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

D) heterocyclic compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, ametoctradin, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quinoxyfen, triazoxide, tricyclazole, 2-butoxy-6-iodo-3-propyl-chromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo[1,5-a]pyrimidine;

E) carbamates thio- and dithiocarbamates: ferbam, mancozeb, maneb, metam, methasulphocarb, metiram, propineb, thiram, zineb, ziram;

carbamates: benthiavalicarb, diethofencarb, iprovalicarb, propamocarb, propamocarb hydrochlorid, valifenalate and N-(1-(1-(4-cyano-phenyl)ethanesulfonyl)-but-2-yl) carbamic acid-(4-fluorophenyl) ester;

F) other active substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tebufloquin, tolylfluanid, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Examples for growth regulators are:

Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole.

Examples for herbicides are:

acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate (e.g. glyphosate free acid, glyphosate ammonium salt, glyphosate isopropylammonium salt, glyphosate trimethylsulfonium salt, glyphosate potassium salt, glyphosate dimethylamine salt), glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy-acetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2- cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

Examples for insecticides are:
organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;
GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
macrocyclic lactone insecticides: abamectin, emamectin, milbemectin, lepimectin, spinosad, spinetoram;
mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon;
Uncouplers: chlorfenapyr;
oxidative phosphorylation inhibitors: cyhexatin, diafenthiuron, fenbutatin oxide, propargite;
moulting disruptor compounds: cryomazine;
mixed function oxidase inhibitors: piperonyl butoxide;
sodium channel blockers: indoxacarb, metaflumizone;
others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

The compositions according to the invention are suitable as herbicides. They are suitable as such or as an appropriately formulated composition. The compositions according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

Depending on the application method in question, the compositions according to the invention can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Brassica juncea, Brassica campestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihotes-culenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays*.

Preferred crops are: *Arachis hypogaea, Beta vulgaris* spec. *altissima, Brassica napus* var. *napus, Brassica oleracea, Brassica juncea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera* and *Zea mays*

The compositions according to the invention can also be used in genetically modified plants, e.g. to alter their traits or characteristics. The term "genetically modified plants" is to be understood as plants, which genetic material has been modified by the use of recombinant DNA techniques in a way that under natural circumstances it cannot readily be obtained by cross breeding, mutations, natural recombination, breeding, mutagenesis, or genetic engineering. Typically, one or more genes have been integrated into the genetic material of a genetically modified plant in order to improve certain properties of the plant. Such genetic modifications also include but are not limited to targeted posttranstional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, are particularly useful with the compositions according to the invention. Tolerance to classes of herbicides has been developed such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase (PPO) inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Examples of these herbicide resistance technologies are also described in US 2008/0028482, US2009/0029891, WO 2007/143690, WO 2010/080829, U.S. Pat. No. 6,307,129, U.S. Pat. No. 7,022,896, US 2008/0015110, U.S. Pat. No. 7,632,985, U.S. Pat. No. 7,105,724, and U.S. Pat. No. 7,381,861, each herein incorporated by reference.

Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflow-ers (DuPont, USA) being tolerant to sulfonyl ureas, e. g. tribenuron. Genetic engineer-ing methods have been used to render cultivated plants such as soybean, cotton, corn, beets and rape, tolerant to herbicides such as glyphosate, dicamba, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecti-cidal proteins of bacteria colonizing nematodes, e. g. Photorhabdus spp. or Xenorhabdus spp.; toxins produced by animals, such as scorpion toxins, arachnid toxins, wasp toxins, or other insect-specific neurotoxins; toxins produced by fungi, such Streptomy-cetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are dis-closed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphino-thricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, Knock-Out®, Bite-Gard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsan-to Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e. g. potato culti-vars, which express resistance genes acting against Phytophthora infestans derived from the mexican wild potato Solanum bulbocastanum) or T4-lyso-zym (e.g. potato cultivars capable of synthesizing these proteins with increased resistance against bacteria such as Erwinia amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Furthermore, it has been found that the compositions according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval in which the individual cotton plants mature leads to an increased fiber quality after harvesting.

The compositions according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

The herbicidal compositions according to the present invention can be applied pre- or post-emergence, or together with the seed of a crop plant. It is also possible to apply the compounds and compositions by applying seed, pretreated with a composition of the invention, of a crop plant. If the active compounds A and C and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active compound are from 0.0001 to 3.0, preferably 0.01 to 1.0 kg/ha of active substance (a.s.), depending on the control target, the season, the target plants and the growth stage. To treat the seed, the compounds I are generally employed in amounts of from 0.001 to 10 kg per 100 kg of seed.

The present invention also relates to a use of the alkoxylate of the formula (I) for reducing the wind drift of an aqueous composition comprising a pesticide (e.g. dicamba).

The present invention offers various advantages: it reduced spray drift fines and off-target movement of pesticide (e.g. dicamba) applications compared to current available formulations, while maintaining use friendly handling and use characteristics, and without adversely affecting their pesticidal activity. The compositions reduced driftable fines at a lower adjuvant use rate in the spray tank in comparison to commercial standard applied as a tank mix. Further advantages of the invention are good adhesion of the pesticide on the surface of the treated plants, increased permeation of the pesticides into the plant and, as a result, more rapid and enhanced activity. An advantage is the low toxicity of the alkoxylates, in particular the low aquatic toxicity. Another advantage is the low harmful effect against crop plants, i.e., low phytotoxic effects. Another advantage is that the volatility of pesticides (e.g. auxin herbicides like dicamba, or 2,4-D) is reduced; or that no additional drift control agent needs to be added to the tank mix, thus allowing an easy and safe preparation of the tank mix.

The invention is further illustrated but not limited by the following examples.

EXAMPLES

Antidrift A: Ethoxylated Cetyl/Oleylalcohol (degree of ethoxylation about 3), HLB about 6.6 according to Griffin.

Antifoam: Aqueous, nonionic silicone emulsion, solid content about 32%.

Example 1

Preparation of SL Formulation

A clear, homogenous aqueous formulation was prepared by mixing 84 wt % of an aqueous solution containing 600 g/l of dicamba BAPMA salt (resulting in 480 ae g/l dicamba), 13.2 wt % Antidrift A, 0.05 wt % Antifoam, and water up to 100 wt %.

The formulation was storage stable for at least three months at 25° C., 40° C. and 50° C. and through 5 cycles of freeze that −20 to 5° C.

Example 2

Sprayable Tank Mix

A sprayable tank mix was prepared by mixing 84.0 ml Roundup WetherMax® from Monsanto (aqueous SL formulation containing 49 wt % potassium glyphosate), 47.2 ml of the dicamba formulation of Example 1, and 3.67 l of water.

The amount of spray drift is influenced by the amount of fine particles from the spray nozzle tip. Typically, spray particles of less than 150 μm in size have a significant higher potential to remain in the air and to be less affected by wind to be carried off-site.

The tank mix was sprayed at 40 psi through a TeeJet AIXR11004 spray nozzle at field dilution rate of 10 gallons per acre (GPA). A laser diffraction setup (SprayTec, Malvern Instruments, 750 mm lens) was used to measure the volume fraction of droplets less than 150 μm in diameter. The laser was positioned perpendicular to the plane of the liquid sheet produced by the spray nozzle. The spray sheet was moved through the laser beam at a constant speed of 4.5 m/s to enable measurements covering the complete width of the spray pattern at a distance of 12" below the nozzle tip. The cabinet in which the experiment was carried out was ventilated at the bottom resulting in a downward air flow of 5.5 km/h. Each sample was passed through the laser three times. Before each pass a new background was collected. The data from the three passes was averaged. The percentage of fines (particle size below 150 μm) was 5%.

For comparison, the dicamba formulation of Example 1 was prepared without the addition of Antidrift A and used for preparing a sprayable tank mix as described above. The percentage of fines (particle size below 150 μm) was 10.5%. Thus, the percentage of fines was reduced by 50% by the addition of Antidrift A.

We claim:

1. An aqueous composition comprising dicamba and a drift control agent, wherein dicamba is present in form of a dicamba polyamine salt and the polyamine has the formula (A1)

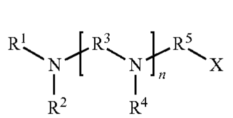

(A1)

wherein $R^1$, $R^2$, $R^4$, $R^6$, and $R^7$ are independently H or $C_1$-$C_6$-alkyl, which is optionally substituted with OH, $R^3$ and $R^5$ are independently $C_2$-$C_{10}$-alkylene, X is OH or $NR^6R^7$, and n is from 1 to 20;

or the formula (A2)

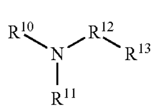

(A2)

wherein $R^{10}$ and $R^{11}$ are independently H or $C_1$-$C_6$-alkyl, $R^{12}$ is $C_1$-$C_{12}$-alkylene, and $R^{13}$ is an aliphatic $C_5$-$C_8$ ring system, which comprises either nitrogen in the ring or which is substituted with at least one unit $NR^{10}R^{11}$; and wherein the drift control agent is an alkoxylate of the formula (I)

$$R^a—O—(C_mH_{2m}—O)_n—H \quad (I)$$

wherein $R^a$ is $C_8$-$C_{22}$-alkyl and/or -alkenyl, m is 2, 3, 4 or a mixture thereof, and n is from 1 to 15.

2. The composition as claimed in claim 1, wherein dicamba is present in form of a N,N-bis(3-aminopropyl) methylamine salt.

3. The composition as claimed in claim 1, wherein the drift control agent is an alkoxylate of the formula (I), wherein $R^a$ is $C_{12}$-$C_{20}$-alkyl and/or -alkenyl, m is 2, a mixture of 2 and 3, or a mixture of 2 and 4, and n is from 2 to 8.

4. The composition as claimed in claim 1, wherein the drift control agent is an alkoxylate of the formula (I), wherein $R^a$ is $C_{16}$-$C_{18}$-alkyl and/or -alkenyl, m is 2, and n is from 2 to 5.

5. The composition as claimed in claim 1, containing at least 300 g/l acid equivalents of dicamba.

6. The composition as claimed in claim 1, containing from 5 to 30 wt % of the drift control agent.

7. The composition as claimed in claim 1 in form of an homogenous solution.

8. A method for preparing a tank mix, which comprises the step of contacting water and the composition according to claim 1, and optionally further pesticides.

9. The method according to claim 7, wherein the tank mix contains up to 3 wt % of the aqueous composition.

10. The method according to claim 8, wherein the tank mix contains up to 0.5 wt % of the drift control agent.

11. A method of controlling undesired vegetation, wherein the composition according to claim 1 is allowed to act on the respective pests, their environment or the plants to be protected from the respective pest, on the soil and/or on undesired plants and/or the crop plants and/or their environment.

12. The method of claim 11, wherein in the alkoxylate of the formula (I), $$R^a—O—(C_mH_{2m}—O)_n—H \quad (I)$$

wherein $R^a$ is $C_8$-$C_{22}$-alkyl and/or -alkenyl, m is 2, 3, 4 or a mixture thereof, and n is from 1 to 15, for reducing the wind drift of an aqueous composition comprising a pesticide.

13. The method of claim 11, wherein in the alkoxylate of the formula (I), $R^a$ is $C_{12}$-$C_{20}$-alkyl and/or -alkenyl, m is 2, a mixture of 2 and 3, or a mixture of 2 and 4, and n is from 2 to 8.

14. The method of claim 11, wherein in the alkoxylate of the formula (I), $R^a$ is $C_{16}$-$C_{18}$-alkyl and/or -alkenyl, m is 2, and n is from 2 to 5.

15. The method of claim 11, wherein dicamba is present in form of a N,N-bis(3-aminopropyl)methylamine salt.

16. The method of claim 15, wherein the drift control agent is an alkoxylate of the formula (I), wherein $R^a$ is $C_{12}$-$C_{20}$-alkyl and/or -alkenyl, m is 2, a mixture of 2 and 3, or a mixture of 2 and 4, and n is from 2 to 8.

17. The method of claim 15, wherein the drift control agent is an alkoxylate of the formula (I), wherein $R^a$ is $C_{16}$-$C_{18}$-alkyl and/or -alkenyl, m is 2, and n is from 2 to 5.

18. The method of claim 15, wherein dicamba is present in at least 300 g/l acid equivalents of dicamba.

19. The method of claim 15, wherein the composition contains from 5 to 30 wt % of the drift control agent.

* * * * *